United States Patent [19]

Girard et al.

[11] Patent Number: 4,654,424
[45] Date of Patent: Mar. 31, 1987

[54] METHOD FOR PREPARING HALOGENATED HYDANTOINS

[75] Inventors: Theodore A. Girard, Williamsport; Lloyd C. Franklin, Montgomery, both of Pa.

[73] Assignee: Glyco Inc., Williamsport, Pa.

[21] Appl. No.: 778,541

[22] Filed: Sep. 20, 1985

Related U.S. Application Data

[62] Division of Ser. No. 465,175, Feb. 2, 1983, Pat. No. 4,560,766.

[51] Int. Cl.⁴ .............................................. C07D 233/72
[52] U.S. Cl. ........................................ 548/311; 8/107
[58] Field of Search ............................ 548/311; 8/107

[56] References Cited

U.S. PATENT DOCUMENTS

| | | | |
|---|---|---|---|
| 3,412,021 | 11/1968 | Paterson | 514/245 |
| 4,102,799 | 7/1978 | Finck | 252/99 |
| 4,242,216 | 12/1980 | Daugherty et al. | 252/103 |
| 4,537,697 | 8/1985 | Girard | 252/90 |

*Primary Examiner*—Richard A. Schwartz
*Attorney, Agent, or Firm*—Cushman, Darby & Cushman

[57] ABSTRACT

A halogenated hydantoin product and method of producing same for use as e.g. a bleaching agent or disinfectant comprising a halogenated hydantoin of the formula

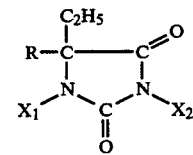

wherein R is methyl or ethyl and $X_1$ and $X_2$ which may be the same or different are chlorine or bromine, either as the sole constituent or in admixture with halogenated dimethylhydantoins. The products are substantially dust-free, free-flowing and upon compaction form a solid product of high physical integrity.

7 Claims, No Drawings

METHOD FOR PREPARING HALOGENATED HYDANTOINS

This is a division of application Ser. No. 465,175, filed Feb. 9, 1983, now U.S. Pat. No. 4,560,766.

BACKGROUND OF THE INVENTION

The present invention relates to halogenated hydantoin products which may be used to produce low dusting powders, granules, briquettes, tablets, and other forms by mechanical compaction, and casting from a melt. The present halogenated products also may be in the form of castings, flakes and products made by treating inert carriers with the halogenated hydantoins in a melt condition. More specifically, the present invention relates to halogenated ethylhydantoins (hereinafter referred to as "HEH") either as sole constituent or in admixture with a halogenated dimethylhydantoin (hereinafter referred to as "halo DMH") so as to produce the product forms enumerated above. As used herein, "HEH" or halogenated ethylhydantoin refers to compounds of the formula

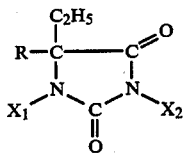

wherein R is methyl or ethyl and $X_1$ and $X_2$ which may be the same or different are chlorine or bromine. The present invention also contemplates utilizing the HEH in admixture with halo DMH, an active chlorine compound and/or an inert carrier in an amount sufficient to produce the desired end product, e.g. powders, granules, flakes, compacted forms, cast forms, etc.

A distinct need presently exists in bleaching, dishwashing, toilet bowl disinfection and water treatment applications (e.g. cooling water treatment, spa and swimming pool disinfection) for halogenated hydantoins in the form of dust-free powders, granules and shaped forms of high integrity. As used herein, the term "high integrity" is meant to refer to solid products having a predetermined shape (e.g. tablets, granules, flakes, briquettes or the like) which are hard, shape-retentive structures and which, for all intents and purposes, are dust-free. A need for such dust-free forms of halogenated hydantoins exists particularly in light of environmental and safety considerations. Halogen donor compounds are irritating in nature. If such products exhibit a large amount of dusting, they are undesirable for use in the home as well as in industrial environments, e.g. for bleaching or dishwashing purposes. Additionally, a high dusting product tends to intensify the halogen odor normally associated with halogen donor compounds. Such a halogen odor can, in and of itself, be most irritating, and should be avoided.

Halogenated derivatives of dimethylhydantoin (e.g. 1,3-dibromo-5,5-dimethylhydantoin; 1-bromo-3-chloro5,5-dimethylhydantoin and 1,3-dichloro-5,5-dimethylhydantoin) are halogen donors typically utilized for various purposes. Thus, 1-bromo-3-chloro-5,5-dimethylhydantoin used for swimming pool sanitizers, while 1,3-dichloro-5,5-dimethylhydantoin has been used successfully for bleaching (see, Kirk-Othmer, Encyclopedia of Chemical Technology, Volume 12, pp. 704–705, Wiley Interscience (1980); and U.S. Pat. No. 2,779,764 to Patterson). However, such halogenated derivatives of dimethylhydantoin are fine, dusty powders which are difficult to compact into solid forms of high integrity or to granulate. Compaction of 1,3-dichloro-5,5-dimethylhydantoin has been proposed in U.S. Pat. No. 4,242,216 to Daugherty et al, the entire disclosure of which is incorporated herein by reference. In practice, however, it has been found that compaction of 1,3-dichloro-5,5-dimethylhydantoin without binders or additives fails to produce solid forms of high integrity which are commercially desirable and alleviate the dusting problems normally attributable to such solid, physically unstable forms thereof.

Typically, when it is desired to produce commercially acceptable forms of a halogenated dimethylhydantoin, a binder of certain polyvalent metallic cations, for example, those of aluminum, zinc, tin, iron, chromium, magnesium and silicon, is utilized to "cement" the halo DMH into a useable form (see, e.g. U.S. Pat. No. 3,412,021 to Patterson). However, use of such binders necessarily increases the cost of the halogenated hydantoin product, which cost is passed onto the ultimate consumer. Moreover, such "binders" do not alleviate the dust problem to the degree now realized by the present invention nor provide durable forms or shapes without the use of additives by simple compaction in the dry state.

Problems also exist when attempting to produce solid halo DMH products blended with other materials by high temperature and melt techniques. Such techniques are not feasible with halo DMH due to the high melting ranges of the materials which are relatively close to the decomposition temperatures of the materials as noted in Table 1 below.

TABLE 1

Melting Point and Decomposition Properties Halogenated DMH

|   | Melting Range °C. | Decomposition Temperature °C.[a] |
|---|---|---|
| 1. 1,3-Dibromo-5,5-dimethylhydantoin | 177–184 | 186[b] |
| 2. 1-Bromo-3-chloro-5,5-dimethylhydantoin | 158–165 | 160[c] |

[a]Initiation of an exothermic decomposition when a 3 gram sample is placed in a test tube immersed in an oil bath and heated at a rate of 1–3° C./min.
[b]vapor forms at 160° C.
[c]vapor forms at 156° C.

Thus, the narrow temperature range between melting and decomposition of halo DMH derivatives renders such compounds unsuitable for producing commercially acceptable products utilizing techniques involving high temperatures.

Accordingly, it is a primary object of the present invention to provide a method of producing halogen donating hydantoin compounds in the form of low dusting powders or granules, thereby minimizing the irritation normally associated with active halogen compounds.

It is yet a further object of the present invention to provide halogenated hydantoins which can easily be handled by the consumer, both industrial and domestic, with little or no risk of eye, skin and respiratory irritation.

Still yet another object of the present invention is to provide halogenated hydantoins which can readily and easily be shaped into a solid product form having high integrity.

These and other advantageous aspects of the present invention will become more clear to the reader after careful consideration is given the description thereof which follows together with the accompanying examples.

DETAILED DESCRIPTION OF THE INVENTION

In accordance with the present invention there is provided a novel method for producing low-dusting powder, granular and shaped forms (e.g. tablets, briquettes or the like) of halogenated hydantoins. The unexpected results of the present invention are realized utilizing the desirable properties of halogenated ethyl hydantoins having the formula

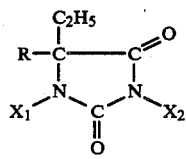

wherein R is methyl or ethyl and $X_1$ and $X_2$ which may be the same or different are chlorine or bromine (sometimes referred to as HEH herein). The present invention contemplates a method for the production of a free-flowing, non-dusting halogenated hydantoin product which comprises halogenating under controlled (i.e. maintaining relatively constant) pH conditions of from 6.0 to about 8.0 (preferably about 6.5 to 7.5) a hydantoin of the formula

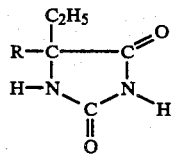

wherein R is methyl or ethyl; to form a precipitate and thereafter filtering, washing, and drying the material to obtain a product which may be characterized as non-dusting and free-flowing. Desirably, halogenation is carried out at a temperature of from about 10° to 30° C.

The invention further provides for shaping the HEH products to form shape-retentive non-dusting forms such as blocks, briquettes, granules etc. without the aid of a binder. The HEH lends itself to blending with other active halogen compounds, particularly chlorine substituted ones to form products useful for a variety of applications including inter-alia disinfection and bleaching.

The term "non-dusting" as used herein, refers to the compounds of the present invention which exhibit little to no dusting as compared to the prior art compounds such as halogenated dimethylhydantoin.

HEH possesses significant properties which are substantially different from those of the corresponding halo DMH compounds. Most noteworthy of such properties is the temperature spread between the melting point, typically in range of between about 60° C. to about 70° C., and the decomposition temperature, typically in the range of between about 150° C. to about 170° C. The significant spread between melting and decomposition temperatures of HEH enhances solid product formation by fusing or casting techniques. Thus, in accordance with the present invention, fusing and casting of HEH products are made possible using techniques at elevated temperatures sufficient to melt the HEH and therefore mold same, but significantly below the decomposition temperature thereof.

Microscopic examination reveals that HEH products of the present invention have a larger particle size and a more crystalline nature than the corresponding halo DMH compounds. Therefore HEH products can be pressure compacted into hard, extremely physically stable forms (e.g. extremely low dusting) without the need for special binders and/or "cementing agents" which the prior art has heretofore thought were absolutely necessary to produce commercially acceptable products. Use of halo DMH compounds alone does not yield such advantageous and surprising results.

As a further embodiment, mixtures of HEH and halo DMH can be prepared either by mixing DMH and either diethylhydantoin (DEH) or 5-methyl-5-ethyl-hydantoin (MEH) in the desired, predetermined quantities prior to halogenation thereof. Alternatively, mixtures can be prepared in situ from the corresponding ketones, acetone, diethylketone and methylethylketone, by utilizing the well known Bucherer-Bergs synthesis, and thereafter halogenating the product utilizing controlled pH conditions in accordance with the present invention.

Proper selection of the ratio of DMH to HEH in accordance with the present invention enhances the end product form desired. HEH unlike halogenated DMH, is useful for making low-dust powders, granules, tablets, flakes, compacted forms, cast forms, and carrier-coated products. Halogenated DMH per se cannot be used for any of the above purposes without the aid of a binder. However, halogenated DMH can be mixed with HEH to yield compositions useful for making all of the above forms. It is only necessary to select the proper ratio of the above forms to achieve the results desired. For example, the following ratios are useful in manufacturing the product forms shown.

|  | DMH Compound | | MEH Compound | |
| --- | --- | --- | --- | --- |
|  | Type* | Moles | Type* | Moles |
| Briquette | B,C | 0.9 | B,C | 0.1 |
| Tablet | B,C | 0.9 | B,C | 0.1 |
|  | C,C | 0.9 | C,C | 0.1 |
| Flake | B,C | 0.5 | B,C | 0.5 |
|  | C,C | 0.5 | C,C | 0.5 |
| Granule | B,C | 0.9 | B,C | 0.1 |
| Low-dust powder | B,C | 0.9 | B,C | 0.1 |
| Compounded with | B,C | 0.5 | B,C | 0.5 |
| Inert carriers | C,C | 0.5 | C,C | 0.5 |

*B,C = bromochloro
C,C = dichloro

The above are upper levels of DMH that should be used. Of course, the DMH can be reduced to 0 and the same results obtained. Obviously, any lesser amounts of DMH yields equally satisfactory results. In like manner, the HEH materials of the present invention can be blended with inert fillers, other active halogen compounds, materials like paradichlorobenzene, and a host of other materials depending in the desired end use.

As noted, the preparation of HEH is dependent upon controlling (i.e. maintaining) the pH of the desired level during halogenation. This can be done by periodic addition of base, e.g. sodium hydroxide.

The following examples are offered to further illustrate the present invention, but are not to be construed as limiting the scope thereof.

EXAMPLE ONE (Comparative)

Preparation of 1,3-dichloro-5-methyl-5-ethylhydantoin (DCMEH)

DCMEH was prepared in accordance with the Patterson U.S. Pat. No. 2,779,764 procedure by placing 142 grams of 5-methyl-5-ethylhydantoin and 500 ml of distilled water in a 2 liter beaker equipped with stirrer, pH probe and thermometer. The solution was cooled to 10° C. 400 mls of a cooled (10° C.) 20% solution of NaOH were added to the MEH/water mixture. 176.3 grams of chlorine was added to the mixture over a period of about 2.5 hours. The pH of the reaction mixture was monitored and rose from pH=9 initially to a high pH=13.9 and finally dropped to pH=7.2 at the conclusion of the reaction. The product, after vacuum filtering, washing and drying, weighed 194.7 grams. It analyzed active halogen as Cl+ =33.4%. The product was a dusty powder and possessed a noticeable chlorine odor.

EXAMPLE TWO (Comparative)

Preparation of DCMEH

In accordance with the procedure outlined in Wolf et al, U.S. Pat. No. 2,090,997, 79.5 grams of sodium carbonate and 771.3 mls of water were charged to a 2 liter beaker equipped with a stirrer, thermometer, pH probe and subsurface chlorine inlet tube. The mixture was stirred to dissolve the sodium carbonate whereupon 71.1 grams of MEH were added with stirring until it also dissolved. The resulting solution pH=9.78 was warmed to 30° C. and 82.5 grams of chlorine gas slowly passed to the mixture until the pH dropped to 7.05. The product precipitated as a semi-solid amorphous mass which hardened into clumps. The solid slurry was vacuum filtered, washed and dried yielding 98.3 grams.

EXAMPLE THREE

Preparation of DCMEH-Controlled pH=6.5

142.2 grams of MEH were dissolved in 2700 mls of distilled water in a 4 liter beaker equipped with a stirrer, thermometer, pH probe, chlorine gas inlet tube and sodium hydroxide addition funnel. The solution was warmed to 40° C. to dissolve the MEH and then cooled to 22° C. 156.6 grams of chlorine gas were added slowly to the mixture over a period of about 1 hour and 50 minutes while maintaining the temperature between about 22°–24° C. and the pH at about 6.5 through the periodic addition of a 20% sodium hydroxide solution. The precipitated product was filtered, washed and dried to a weight of 197.7 grams. The analysis of the product for active halogen as Cl+ was 33.5%. The material was free flowing with no apparent dusting or irritating halogen odor.

EXAMPLE FOUR

Free-Flow Characteristics

The flow characteristics of the DCMEH products of Examples One and Three were compared by determining the angle of repose for each product. Into two 4 oz. jars were charged twenty-two grams of the DCMEH products of Examples One and Three. The jars were both capped. Each jar was tapped by raising the jar one inch off the table and then dropping. The jars were then tipped on their side and the angle of repose (i.e. the angle between the table and the sample incline) determined. The product of Example One did not flow, but rather remained stuck to the bottom of the jar. The DCMEH product of Example Three flowed into an angle of 45° with relation to the horizontal. The angle of repose clearly illustrates the free flowing nature of the products of the present invention.

The angle of repose of the product is not critical, but is merely a means of evaluating flow characteristics. No flow would exhibit a 90° angle with the horizontal. Thus, products of the present invention should exhibit an angle of less than 90° (e.g. less than 70°) and readily flow to form an incline with the horizontal. The sample should not compact or cling to the bottom or walls of the container.

A free-flowing product is essential for manufacturing tablets and compacting forms. It will be appreciated that any material which is to be compacted or tableted must flow freely into die cavities and into the pockets of compacting rolls. The material must be able to flow freely from containers, feed hoppers and to be screw-conveyed without bridging, sticking or holding-up in the equipment.

EXAMPLE FIVE

Dusting Characteristics

The HEH products of the present invention are further characterized by their low-dusting properties. This example illustrates the relative dusting properties of DCMEH prepared according to the present invention when compared to other materials.

Apparatus was set up to determine the relative dusting characteristics of HEH materials. The apparatus consisted of a 16 inch diameter cylinder (24.25 inches high) having a slot in the side approximately 1 inch wide×8 inches long (starting 6 inches up from the bottom). A large piece of filter paper (Whatman 32 cm #1) is placed on the bottom of the container. On the filter paper (in the center) was placed a 100 mm×10 mm petri dish. A plastic funnel (4.25 inch OD top×0.75 inch OD bottom) was sligned directly above a 13/16 inch diameter×4 inch glass tube held with the aid of ring clamps and positioned 8 inches above the petri dish.

The DCMEH samples of Examples One and Three were evaluated independently for dustiness. 2.5 grams of DCMEH samples from Examples One and Three were placed in a 50 ml beaker. The samples were dumped quickly (with a moderate tap on the funnel) into the funnel. The petri dish containing most of the sample was removed and the filter paper placed on a clean level surface. Using an atomizer sprayer, the filter paper was then sprayed with a 15% aqueous solution of potassium iodide and allowed to dry. Against a black background, the filter paper which was placed beneath the DCMEH of Example One revealed dusting over its entire surface. By contrast, little dusting was evidenced on the paper placed under the material of Example Three.

As can be seen the HEH material of the present invention exhibits significantly little dusting.

EXAMPLE SIX

Preparation of DCDEH

A sample of 1,3-dichloro-5,5-diethylhydantoin was prepared by chlorinating 51.5 grams of diethylhydantoin (obtained from the reaction of 3-pentanone, potassium cyanide and ammonium carbonate at 60° C.) and 57.4 grams of chlorine gas at a controlled pH of 7.15 to 7.5 using 20% solution of sodium hydroxide at a temperature of 15°–23° C. The reaction was carried out in the same manner as Example Three to yield 69.1 grams of DCDEH having an analysis of total halogen=30.7. The product was free flowing and had little chlorine odor. MP=44.5.48° C. Decomposition Temperature=151° C.

EXAMPLE SEVEN

Preparation of BCDEH

Bromochloro-5,5-diethylhydantoin was prepared by charging 39 grams DEH, 25.7 grams sodium bromide and 1117.4 mls of distilled water to a two liter flask equipped as in Example Three. The mixture was then chlorinated with 45.2 grams of chlorine at a controlled pH of 7.3–7.60 using a 20% solution of NaOH at a temperature of 16°–24° C. The product was filtered, washed and dried as in Example Six to yield 63.0 grams of a free-flowing low-dusting product having an analysis of total halogen=59.3%; MP=82°–96° C.; Decomposition Temp.=139° C.

1,3-Dichloropentamethylene and 1,3-dichloro-5,5-diphenylhydantoin were also prepared according to the present method. However, due to the small difference between the melting point and decomposition temperature of these materials, they are not suitable for the present invention.

While the present example utilized NaBr to generate bromine, it will be appreciated that elemental bromine may be employed in a manner similar to the use elemental chlorine above.

EXAMPLE EIGHT

HEH Melt Blends

A mixture of 0.5 moles of dimethylhydantoin (DMH), 0.5 moles methylethylhydantoin (MEH) and 0.5 sodium bromide was chlorinated in accordance with the procedure of Example Seven. The halogenated MEH/DMH product had a melting range of 65°–121° C. and a decomposition temperature of 180° C. The product was fluid at 70° C.

15 grams of the product were melted in a 100 ml beaker over a steam plate, and then 15.0 grams of sodium tripolyphosphate (STP) were blended into the melt with the aid of a stirring rod. Upon cooling the mixture solidified to a free flowing granular product which gave off a light to moderate chlorine odor and exhibited no dusting.

Similarly, 15 grams of the halogenated MEH/DMH product were melt blended with 15 grams of soda ash. The resulting granular product was free-flowing exhibited no dusting and only a light chlorine odor.

Like results were obtained with 50:50 blends of the halogenated MEH/DMH with anhydrous sodium sulfate, talc, Bentolite L, mineral colloid, Zeolite Types 4A and sodium chloride.

EXAMPLE NINE

Combinations of HEH With Active Halogen Compounds

A series of solid melt blend products were prepared by melt blending at 55°–70° C. the halogenated MEH/DMH (referred to below as H-MEH/DMH) material obtained in Example Eight or DCMEH with various active chlorine compounds. The melt blends were allowed to solidify in ice cube trays. The blends included:

| % HEH and type | Active Chlorine Compound |
| --- | --- |
| 90% H-MEH/DMH | 10% sodium dichloroisocyanurate (NaDCC) |
| 70% H-MEH/DMH | 30% NaDCC |
| 50% H-MEH/DMH | 50% NaDCC |
| 90% H-MEH/DMH | 10% trichloroisocyanuric acid |
| 90% DCMEH | 10% Ca(OCl)$_2$ |
| 90% DCMEH | 10% LiOCl |
| 90% H-MEH/DMH | 10% Ca(OCl)$_2$ |

The products exhibited no dusting and gave off light to moderate chlorine odor. These type of products are particularly suitable for applications in spas, swimming pools, urinal or toilet bowels, distinfection where both an immediate and sustained release of halogen is desired.

EXAMPLE TEN

HEH Combined With Paradichlorobenzene

This example illustrates that the HEH materials of the present invention are suitable for preparing urinal blocks from melt blends of HEH and paradichlorobenzene (PDCB).

Ten grams of the H-MEH/DMH material used in Example Nine were melt blended at 54°–55° C. with 10 grams of PDCB in the same manner as outlined in Example Nine to give a slightly yellow cube block which exhibited no dusting and smelled only of PDCB.

Similarly blocks were made by melt blending 5 grams DCMEH and 5 grams PDCB. Again no dusting was evident and only the smell of PDCB observed.

EXAMPLE ELEVEN

Compacted Forms

A series of compacted products were made from the HEH material of the present invention. Durable granules, briquettes, and tablets were produced by the following techniques.

Granules were produced continuously via an integrated roll compaction, granulation and screen classification system. Powder was fed continuously from a feed hopper to a roll compaction machine equipped with rolls to produce sheet compact. The effluent compact was fed by gravity to a Rietz granulator operated under controlled "grind" conditions dictated by the final size granules desired. Effluent from the granulator flowed by gravity to a screen classification system designed to separate granulated material into desired size fractions ranging from less than 6 U.S. Sieve mesh to greater than 200 mesh.

9 cc briquettes were produced directly from the roll compactor cited above using conventional type briquetting rolls. The physical durability of these briquettes was verified by shipping a 40 pound sample approximately 6,000 miles by truck. Less than 2% attrition or breakage was observed as measured by sieving the briquettes through a ¼ inch mesh screen.

13 cc tablets were also produced continuously utilizing a rotary tableting press.

EXAMPLE TWELVE

Products were prepared utilizing various quantities of DMH, MEH and NaBr and the procedures outlined in Example Seven. Such products were examined for their physical characteristics, the results being recorded in Table 2 below.

TABLE 2
Halogenated Hydanioins

| Product No. | Moles DMH | Moles MEH | Moles NaBr | Melting Range (°C.) | Decomposition Temp. (°C.) |
|---|---|---|---|---|---|
| 1*A | 1.0 | 0.0 | 0.0 | 132–134.5 | 191 |
| 2*B | 1.0 | 0.0 | 1.0 | 158–165 | 160 |
| 3C | 0.0 | 1.0 | 0.0 | 60–64 | 170 |
| 4D | 0.0 | 1.0 | 1.0 | 74–79 | 148 |
| 5 | 0.8 | 0.2 | 0.5 | 128–142 | 180 |
| 6 | 0.8 | 0.2 | 0.8 | 146–163 | 180 |
| 7 | 0.8 | 0.2 | 1.0 | 139–157 | 171 |
| 8 | 0.5 | 0.5 | 0.5 | 65–121 | 180 |
| 9 | 0.5 | 0.5 | 0.8 | 73–133 | 155 |
| 10 | 0.5 | 0.5 | 1.0 | 73–139 | 167 |
| 11 | 0.2 | 0.8 | 0.5 | 59–68 | 176 |
| 12 | 0.2 | 0.8 | 0.8 | 69–88 | 145 |
| 13 | 0.2 | 0.8 | 1.0 | 71–95 | 160 |

| Product No. | Appearance | Dusting |
|---|---|---|
| 1*A | Fine Powder | Heavy |
| 2*B | Fine Powder | Heavy |
| 3C | Grainy Powder | Medium |
| 4D | Grainy Powder | Medium |
| 5 | Granular | Trace |
| 6 | Semi-Granular | Trace |
| 7 | Grainy Powder | Medium |
| 8 | Granular | Trace |
| 9 | Grainy Powder | Light |
| 10 | Grainy Powder | Trace |
| 11 | Granular | Trace |
| 12 | Semi-Granular | Light |
| 13 | Grainy Powder | Light |

| Product No. | Flow-ability | Casta-bility | Flaka-bility | Compaction and Granulation |
|---|---|---|---|---|
| 1 (Comparative) | – | – | – | Poor |
| 2 (Comparative) | – | – | – | Poor |
| 3 | + | + | + | Excell. |
| 4 | + | + | + | Excell. |
| 5 | + | + | + | Excell. |
| 6 | + | + | + | Excell. |
| 7 | + | – | – | Excell. |
| 8 | + | + | + | Excell. |
| 9 | + | + | + | Excell. |
| 10 | + | + | + | Excell. |
| 11 | + | + | + | Excell. |
| 12 | + | + | + | Excell. |
| 13 | + | + | + | Excell. |

*Comparative
A DCDMH
B BCDMH
C DCMEH
D BCMEH

As can be readily appreciated from the above examples and the tabulated data of Table 2, the products of the present invention are more crystalline, granular, free-flowing and exhibit significantly less "dusting" than other halo hydantoins (e.g. compare product Nos. 3–13 to product Nos. 1–2 in Table 2). The halogenated products of the present invention facilitate compaction and the forms thus produced have greater physical integrity (e.g. hardness, resistance to breaking, ease of tableting without "capping", and the like) when compared to other halo hydantoin derivatives.

Moreover, the products of the present invention which include increased amounts of MEH exhibit markedly reduced melting temperatures and a significant differential between such melting temperatures and decomposition temperatures. This increased differential between melting and decomposition temperatures permits formation of final products by fusion or partial melting techniques. Thus, when the melt or partial melt is cast or extruded into forms of the desired shape or flaked by pouring or placing the melt onto a cool surface, product forms result which are physically stable, hard and dust free.

As can be seen from the foregoing examples, the unique properties of the HEH materials permits the manufacture of unique products which would not be otherwise possible. Because of the low melting point of the preferred hydantoins, they may be:

(1) melted, mixed with inert carriers, and then allowed to cool and solidify;

(2) mixed as solids with inert carriers, heated until the hydantoin melts, and then cooled to solidify the hydantoin; and (3) melted and sprayed onto the surface of inert carriers.

The products thus prepared may be either surface coated, or impregnated with the HEH. The products are non-dusting, granular, free flowing. The inert carrier selected is appropriate to the intended end use, e.g., bleaching, scouring powders, diswashing compositions, water treating chemicals, toilet bowl disinfectants and deodorizers. The product characterization can be adjusted to fit the application, e.g., rate of solubility, dispersibility, concentration, compatibility with other formulation ingredients, etc.

While the present invention has been herein described in what is presently contemplated to be the more preferred embodiments thereof, those in the art may appreciate that many modifications may be made hereof, which modifications shall be accorded the broadest interpretation of the appended claims so as to encompass all equivalent methods, processes and/or materials.

What we claim is:

1. A method for the production of a free-flowing, non-dusting halogenated hydantoin product which comprises halogenating under controlled pH conditions of from 6.0 to about 8.0 a hydantoin of the formula $$R-\underset{\underset{H-N}{|}}{\overset{\overset{C_2H_5}{|}}{C}}-\underset{\underset{N}{|}}{\overset{\overset{}{}}{C}}\overset{=O}{\underset{H}{}}$$

wherein R is methyl or ethyl; to form a precipitate and thereafter filtering washing and drying the product characterized as non-dusting and free-flowing and having the formula $$R-\underset{\underset{X_1-N}{|}}{\overset{\overset{C_2H_5}{|}}{C}}-\underset{\underset{N-X_2}{|}}{\overset{\overset{}{}}{C}}\overset{=O}{}$$

wherein R is methyl or ethyl and $X_1$ and $X_2$ which may be the same or different is chlorine or bromine.

2. A method according to claim 1 wherein the pH is controlled at from about 6.5 to 7.5 by the addition, during halogenation, of sodium hydroxide.

3. A method according to claim 1 wherein halogenating is carried out at a temperature of from about 10° to 30° C.

4. A method according to claim 1 wherein the hydantoin is 5,5-diethylhydantoin.

5. A method according to claim 1 wherein the hydantoin is 5-methyl-5-ethylhydantoin.

6. A method according to claim 1 wherein dimethyl hydantion and an alkali metal bromide are present during halogenation, and further that at least one of $X_1$ and $X_2$ is bromine.

7. A method according to claim 1 wherein the product obtained has an angle of repose of less than 70°.

* * * * *